United States Patent [19]

Wagner

[11] Patent Number: 4,600,403

[45] Date of Patent: Jul. 15, 1986

[54] SUCTION INJECTOR II

[75] Inventor: Wolfgang Wagner, Exerzier Str. 1, 1000 Berlin, Fed. Rep. of Germany

[73] Assignee: Wolfgang Wagner, Berlin, Fed. Rep. of Germany

[21] Appl. No.: 405,559

[22] Filed: Aug. 6, 1982

Related U.S. Application Data

[60] Continuation-in-part of Ser. No. 241,378, Feb. 26, 1981, Pat. No. 4,393,870, which is a continuation-in-part of Ser. No. 93,615, Nov. 9, 1979, Pat. No. 4,284,077, which is a division of Ser. No. 933,136, Aug. 14, 1978, abandoned, and a continuation-in-part of Ser. No. 793,951, May 5, 1977, Pat. No. 4,114,691, which is a continuation-in-part of Ser. No. 634,741, Nov. 21, 1975, abandoned.

[51] Int. Cl.$^4$ ............................................. A61M 5/00
[52] U.S. Cl. ..................................... 604/115; 604/186
[58] Field of Search ............... 604/115, 181, 186, 187, 604/218, 207

[56] References Cited

U.S. PATENT DOCUMENTS

| | | | |
|---|---|---|---|
| 4,114,619 | 9/1978 | Wagner | 604/115 |
| 4,139,008 | 2/1979 | Wagner | 604/115 |
| 4,393,870 | 7/1983 | Wagner | 604/115 |

*Primary Examiner*—John D. Yasko

[57] ABSTRACT

A suction injector, particularly for use with hypodermic injections, has a liquid container with a compartment containing pressurized gas, a hose to a cannula into a suction cup, which may be replaced after every use, consisting of an outer chamber with stored underpressure, which works, after a hole is opened by the shifting of supporting tube, moved by the pressure of skin pushing against this supporting tube. The underpressure of the suction cup starts a kind of spring driven roller pump provided with blocking dosing pegs for a multiple dosing choise. A valve for automatic reventilation is provided, as is a blocking and marking mechanism, relating to the emptying of the liquid supply, consisting of a taster finger, engaged in a hose loop, which frees the movement of a spring driven seivel arm against the skin and the suction cup, if the medicine supply is emptied. A revolution counter for the control of therapy is provided.

26 Claims, 21 Drawing Figures

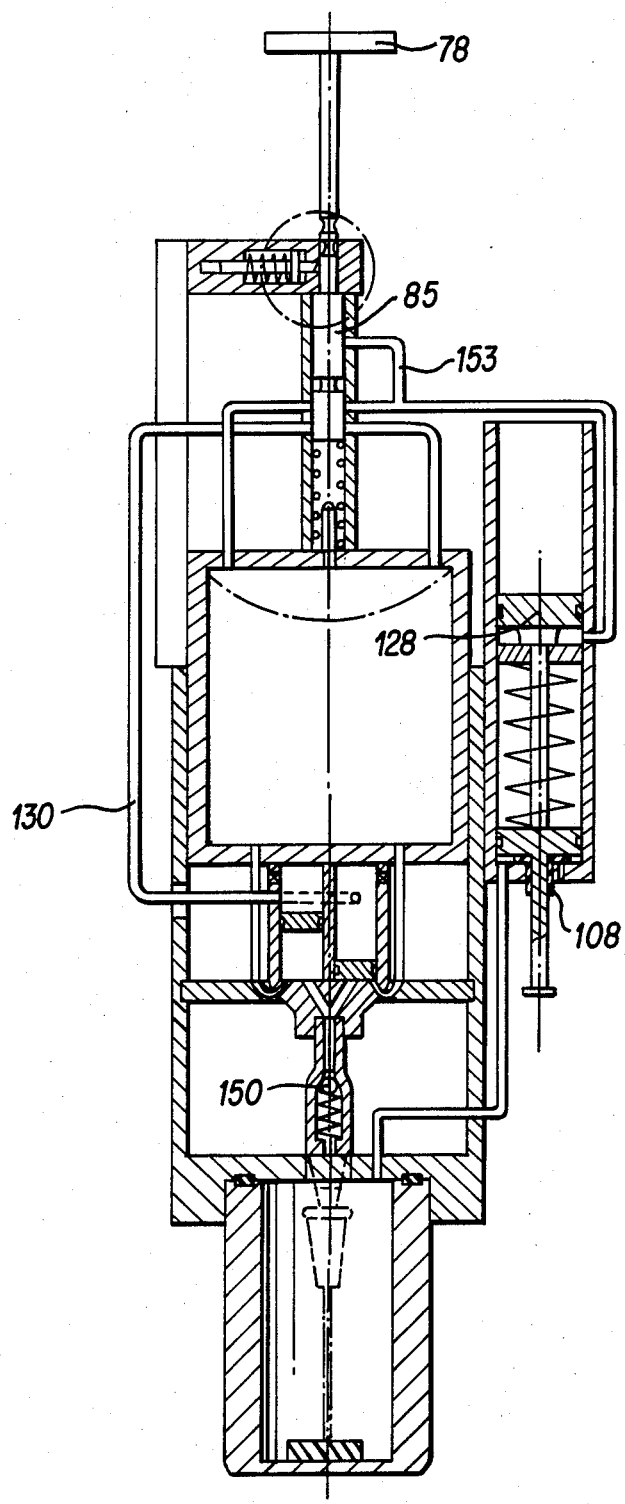
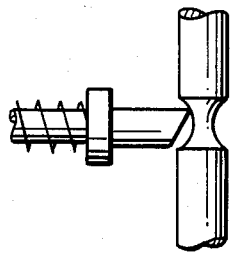
FIG. 2A
FIG. 2
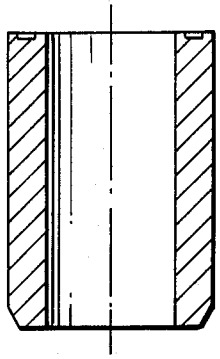
FIG. 2B

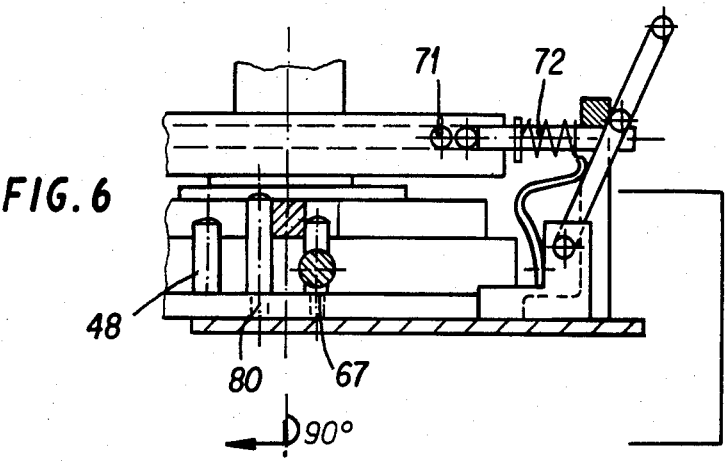
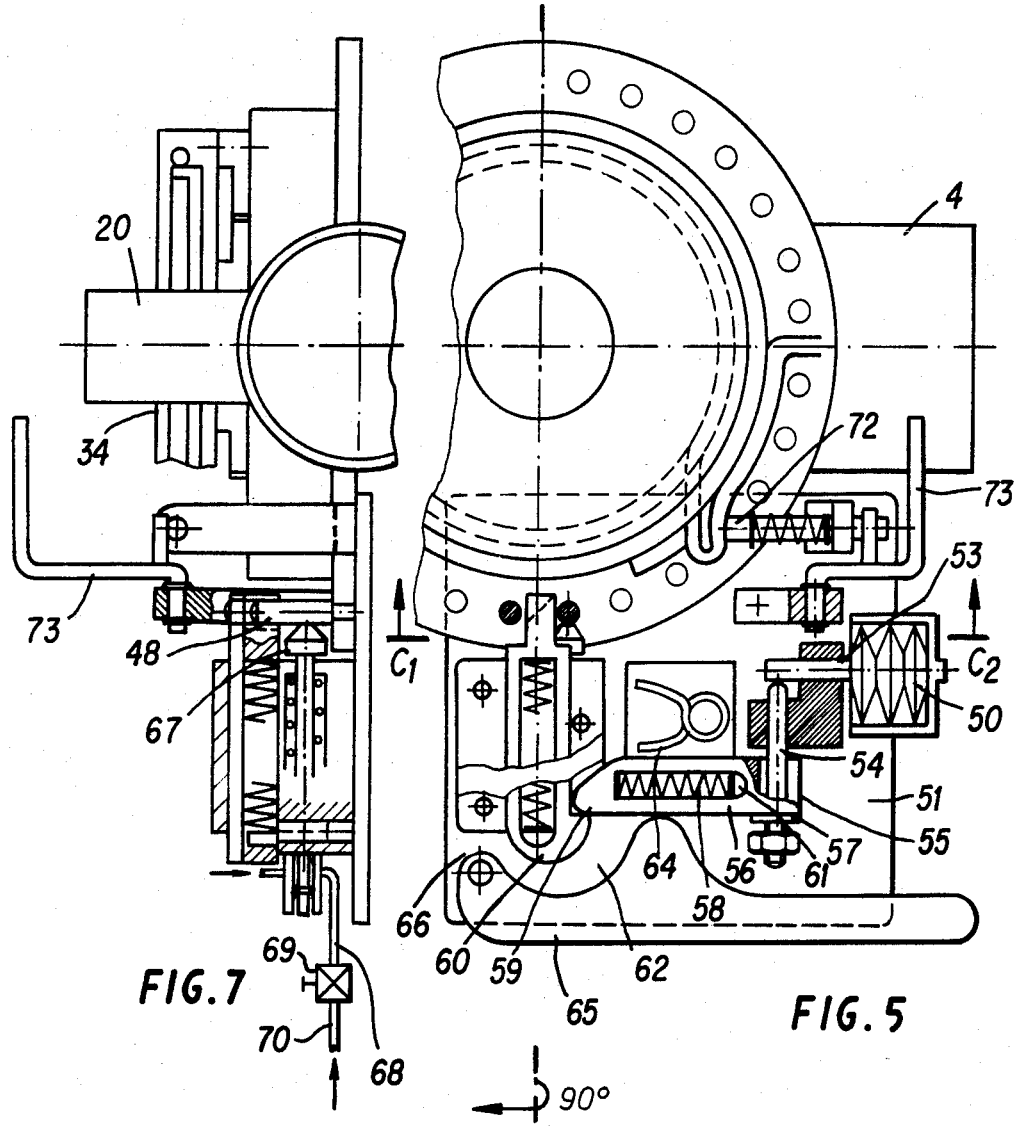

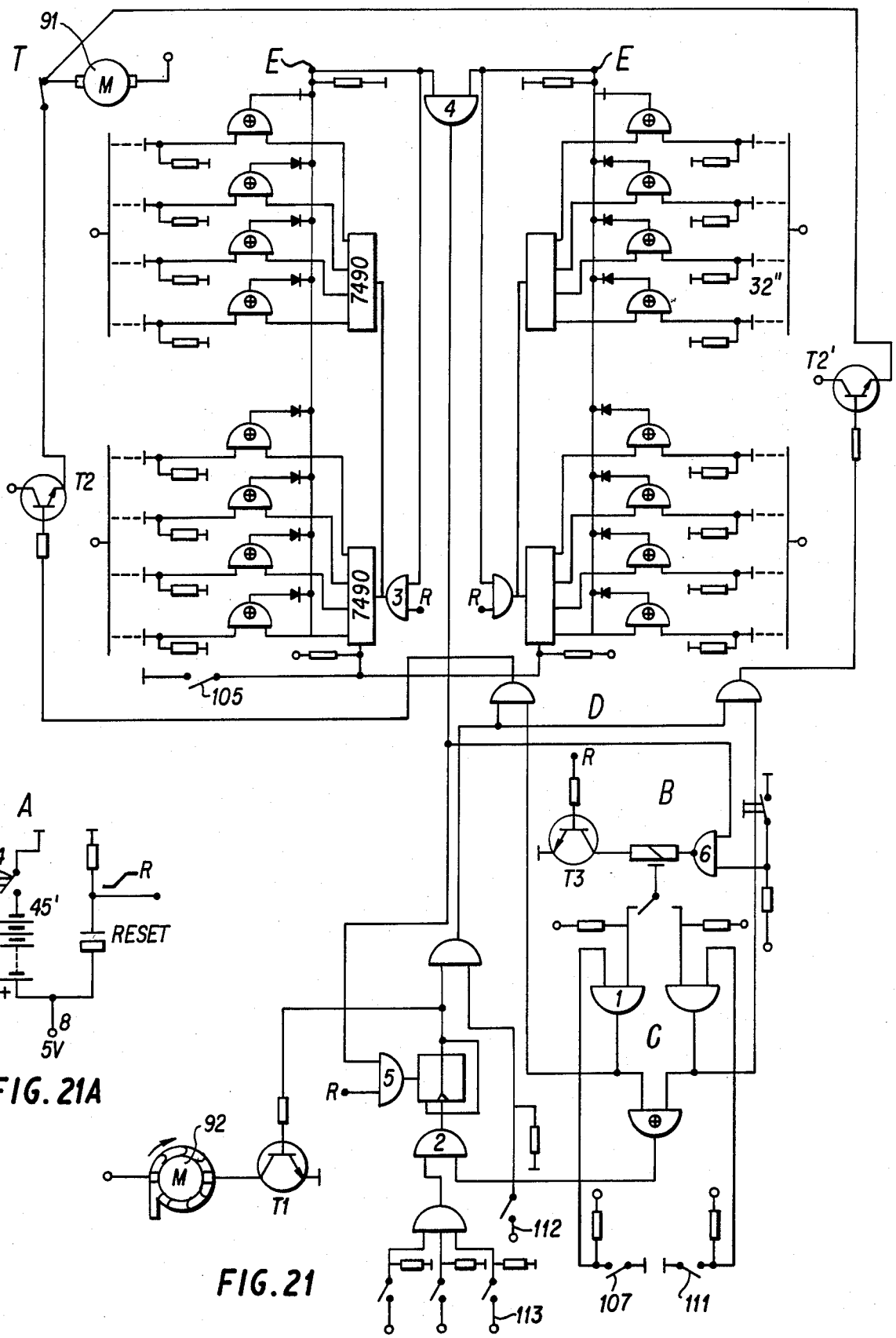

SUCTION INJECTOR II

CROSS-REFERENCE TO RELATED APPLICATIONS

This application is a continuation-in-part of my copending patent application Ser. No. 241,378, filed Feb. 26, 1981, now U.S. Pat. No. 4,393,870, which is a continuation-in-part of my copending patent application Ser. No. 093,615, filed Nov. 9, 1979 now U.S. Pat. No. 4,284,077 which is a divisional application under 37 CFR 1.60 of prior patent application Ser. No. 933,136, filed Aug. 14, 1978 which is now abandoned and is in turn a continuation-in-part of the patent application Ser. No. 793,951, filed May 5, 1977, now U.S. Pat. No. 4,114,691, which in turn is a continuation-in-part of my application Ser. No. 634,741, filed Nov. 21, 1975, now abandoned, and the entire disclosure of which is herewith incorporated by reference. This application is also related to my copending patent applications Ser. No. 618,686, filed Dec. 21, 1975, Ser. No. 634,742, filed Nov. 21, 1975, now abandoned and Ser. No. 639,685, filed Dec. 8, 1975, all of whose disclosures are also herewith incorporated by reference.

BACKGROUND OF THE INVENTION

The present invention relates to medical technology. More particularly, this invention is concerned with an injection apparatus for hypodermic injections wherein a plurality of different liquid medicaments can be used, especially for the self-injection of insulin by diabetics.

Insulin treatment is still characterized by injection from syringes, the insulin being drawn out of small medicine bottles, into which unsterile air is blown in the process, and to which an antibacterial substance has been added. It often happens that small air bubbles with the syringe are overlooked, or, when detected, they can only with difficulty be eliminated by tapping, while the canula is being held with the point upwards. Many patients, particularly when their vision is impaired by age or disease, cannot clearly read the syringe scale. Other patients do not have the strength to overcome the friction of the piston; and still others have serious difficulties, for example, with the lack of friction in long-stroke syringes, in that they unintentionally empty part of the contents. For novices, there are the problems of fear of the needle and clumsiness in handling. The preparation of syringes and the execution of injection have certain spatial and material preconditions. Hitherto existing suction injectors have generally been used on animals. Little regard was made to sterility. Besides that, the devices were too large and difficult to use. Great effort and space were needed to produce the vacuum. There are injection apparatuses for insulin on the market which work by underpressure without a cannula, but they are in reality useless. The pressurized stream of medicine destroys tissue to a considerable extent and leads, when used daily, almost regularly to serious skin irritations. The painfulness of this method exceeds that caused by use of modern cannulas. Besides that, the nozzles become clogged by the protein solution and have to be carefully cleansed. The supply bottles are still filled with unsterile air for the replacement of volume. The recently introduced insulin pumps for the continuous dosing of old insulin promise to be for many years to come a solution of the problem for only a limited group of patients and even then only for limited periods. The pumps, which are carried on the body, require a problematical connection with the blood stream or with the lower skin tissue, for example to the abdominal cavity, thus presenting a potential source of infection. Even devices with sensors for measuring the amount of sugar in the blood implanted in the body, even if they are one day developed to the point where they function perfectly, present the problem, that an automatic dosing of insulin, whenever the level of sugar in the blood rises, would increase the appetite, which itself would have a negative effect on problems, such as overweight and arteriosclerosis, which are connected with diabetes. There is also the danger of hypoglycemia, especially at night, with the consequence of irreparable brain damage. Other hormonal and metabolic variables, as for example the level of lactic acid during muscular exertion, would have to be taken into account. A specified daily routine would have to be programmed, thus limiting further the hoped for greater or complete freedom for the patient's diet.

SUMMARY OF THE INVENTION

The here presented invention, which was developed through experience in internistic medical practice, is designed to avoid these disadvantages. The insulin should be stored in pressure storage bottles, while a gas filled body, optimally a folding bellows, transfers the medication through a tube to the patient. No unsterile air enters the system. The pumps do not have to be cleaned. Instead of the freon $cF\ Cl_3$ (Frigen 11, Hoechst) which is used in spray bottles, greater use should be made of carbon dioxide, which, in the case of leakage after disposal, causes no damage to the environment. For the movement of a stored volume of 50 ml of insulin, for example, 560 mg of sodium hydrogene would be necessary in a folding bellows made of silicone. Wall grooves in the bottle facilitate the outflow of fluid from the folds of the folding bellows. The determination of the dose in the tube occurs by means of the pinching movement of the spring blades along a wheel. The tube is led within a half-moon-shaped groove and is given little room for expansion between the dosing wheel and the wall. The pinching movement corresponds to the reliable procedure, used for decades in pumps for direct blood transfusions and for tube pumps in laboratories. There had, of course, to be technical simplications and financial and spatial reductions. The available systems are too expensive. It was of use, that, when pressure bottles are used, actually only the task of separating the dose has to be accomplished. This is possible by means of spiral springs. Even in medical circles, there has been surprisingly little interest in increasing the reliability of the therapy. This is clearly shown by the lack of interest in works on oral medication control and the technical aids which have been suggested for it. Even insulin is a very dangerous medicine in the hands of a careless or otherwise unsuited patient. Great interest was shown in those aspects of therapy reliability, in which the dosage is made visible by clear demarcation of spaces and besides by measuring lines on the axis rod, the spiral groove of which is intended to facilitate spring tension. A doctor or attendant can at any time determine the total dose by means of a counting meter. When the medicine supply has been exhausted, a swivel arm drops over the suction cup rim and onto the skin as a warning and an obstruction to injection, which cannot be accidentally removed. For dosing, the back and forth movement of a disc with the dose rods, which can be freely interchanged and moved between the standard stages of dosing, is transformed by means of a ratched wheel with pawl. A manually activated auxiliary spring mechanism, which reacts to suction in the suction cup area, was created for triggering in cases of less suction. It is thus prevented, that the medicine is expelled, before the cannula is in position under the skin. When a stronger suction source is used, the dose bar can be directly or indirectly drawn back by means of a suction piston or a folding bellows or briefly by means of a spring blade with a stop nob or—as is standard in pneumatics—by means of a special valve system, which is not dealt with in detail here.

Suction production through a mouthpiece is possible: a check valve prevents a rise in pressure in the suction cup before the completion of the injection. The determination of the right point in time for reventilation was problematical. The problem is solved in this invention in the following manner: the shiftable bolt, which comes to rest before the dose bar, pushes the tapered top of a valve, connected to springs, with its final movements, while the opened ventilation valve leads to the exterior air through a throttle nozzle and thus only gradually reventilates the suction cup, so that the injection procedure can first be terminated. The mechanism for the triggering of the shiftable bolt by means of suction from the suction cup also continues to function, although the ventilation valve only then closes. The throttle nozzle must be very precisely set, if disposable suction cups with industrially reproduced vacuum in a special container are used. Such disposable injectors do not require a special vacuum generator and are improved here by making the cannula or better the cannula shaft a firm and irremovable part of the injector. The necessity of the difficult insertion of the cannula is thus eliminated, and the cannula can be held better, which reduces the danger of an injury through the cannula before or after use. A boring past the funnel for the reception of a syringe cone to inner portion of the disposable injection apparatus can be used to the reventilation after the injection, if it is sealed by a membrane before use. If the membrane is removed before use, and the funnel is connected to the connection fitting with its cannula attachment pipe, then the vacuum, which is transfered out of the outer chamber through the opened valve to the suction cup area, after the supporting tube presses on the skin, is transfered through the channel next to the funnel also to the dose mechanism of the injector, if a sealed tubular connection between the latter and the channel has been established. The valve mechanism between the outer chamber, acting as a large vacuum reservoir, and the inner portion consists here, only as an example, of two lateral openings of the vacuum reservoir and the supporting tube which can be pushed together to meet each other. Production would be rather expensive, and the sealing would require the use of wax or a special coordination of the elasticity between the parts which touch. Other methods and construction characteristics are given in the allowed application Ser. No. 634,741.

A major advantage of the above described injector, which avoids the use of injection syringes is, that the simplication of use, which has been achieved, facilitates for individuals desirable increase in the number of injections with a corresponding reduction of the individual doses. This permits a better metabolic adjustment and reduces the danger of skin irritations and the pain of the individual injections. The education effect on the patient, who has the opportunity outside and even when traveling to receive his insulin without attracting attention or endangering the sterility of the procedure, is of value. It is particularly important for the patient to know when the liquid medicine supply is emptied, especially because the daily and constant usage of the medicine tends to lead to unintentional negligance. A warning device such as the proposed swivel arm is of further advantage to the patient because of its inconspicuousness to others. When the insulin is packed in siliconated glass cylinders, drainage tubes within the cylinders can facilitate the emptying of the folds of a gas-filled folding bellows. In particular, other medicines can be stored in a membranous container, which is compressed from the outside, and put under gas pressure from the outside. In special cases, the wall of a container, filled with pressurized gas, consists of a membrane, but one of limited elasticity, in order to direct the stored gas pressure onto the interior bag with the medicine, which is emptied through the tube and the tube pump into a suction cup or with repeated use into the individual injectors. A combination of fluid and solid substances can also be chosen, which are brought together in special devices or within the gas storing part of a gas pressure bottle, to then produce or compliment gas pressure. A suction producing device such as a suction pump or a jet pump, can also be driven by such a gas source. (See details in the description.)

It is important, particularly with regard to the reliability of life preserving treatment, that, in addition to control by means of counting meter, a blocking mechanism is provided, which indicates to the patient, that the medicine supply has been exhausted. For this purpose, a tracing finger with springs, adjusted to the fluid pressure in a loop of the medicine tube, can be directed against this loop and activate one or more blocking mechanisms, when the fluid pressure in the tube is relaxed. Besides the possibility of a blocking off of the renewed activation of the functions which prepare dosing, a swivel arm, has been deemed useful, which in the case of insufficient dosing snaps during the injection against the skin and then going under the rim of the suction cup, hinders its sealing to the skin. The combination of the given examples of a warning and blocking mechanism permit the determination of the last necessary dosage which was not given, because the supply was exhausted.

Control and security of therapy can also be heightened by providing a transparent, sealable covering plate over the dose rods or a time lock, which would allow injections only after the elapse of certain minimum periods. Such devices, as in the above mentioned examples for oral medication control, can readily be applied to injection therapy. Forgetful and mentally ill diabetics can in this manner be protected against the dangers of hypoglycemia.

In an electrically driven version of the invention, the spiral spring can be replaced by a pace motor, and the dosing pegs by contacts for running, for example, a decimal counter TTL 7490. The dosing wheel can also be driven by means of a coupling by a compressor, which is used for the production of suction in the suction cup. It would seem best in such cases for the signal for the release of medicine to proceed from a contact within the suction cup, which, after being touched by the skin, activates the dose bar or the pace motor in the same manner as a earth or sensor contact switch, as they are used in electric alarm clocks or night lamps.

In the example presented, a single electric motor was used to drive both the dosing wheel by means of a control gear and compressor for the creation of suction instead of using a pace motor. The dosing is carried out in a manner which takes into account a certain sluggishness in the braking of the motor. The technically more elegant magnetic brake was, for the purposes of demonstration, replaced by a centrifugal force regulator. The reventilation takes place through a nozzle in the case, which is connected by means of a channel to the suction cup and serves as a vacuum storer. The switch elements are sealed against the outside air by folding bellows. If electrical energy is to be conserved, the motor is activated by three electrical contacts near the rim of the suction cup, all of which are activated simultaneously by proper positioning on the skin. The injection is triggered by the skin, as soon as it has been raised high enough, by means of a contact rod which is between two cannula attachment cones. The tube which introduces the suction can be lengthened and used as a touch contact for a sensor switch, as for example often used for earth switches on night lamps.

It is most practical (especially when gas storing folding bellows are used), if the gas pressure bottles are provided on the end opposite from the bottle neck with a recess, into which the bottle neck of another medicine pressure bottle with its tube clip and connection fitting can be fitted. The stacking, which thus is made possible saves space for transportation and storage. It is best here, if the tube is wrapped around the connection fitting with its cannula attachment pipe.

An inserted longitudinal channel or a groove on the inside of the container wall can facilitate the flow of liquid out of the folds of the folding bellows. The storage of medicines in a sort of bag with a sealed connection to the hose, which is led into a special holding plate, can also be considered, in which case the fluid bag is positioned inside of another, larger bag, which contains pressurized gas, is relatively inelastic and presses on the fluid bag in such a way, that it can be more easily emptied through the hose. A blocking mechanism for the functioning of the device is shown, in which the tracing finger spring becomes dominant by being touched by the tube, which carries the medicine, after the supply has been used, and, for example, brings a check gear into mesh with a gear of the counting mechanism by means of a pull on the base.

The basic constructional characteristics of the invention can be generally expressed as follows: a suction injector, particularly for use with hypodermic injections, comprising a liquid container with a gas pressurized compartment sealed from said liquid container; a hose connected to said liquid container for the transmission of said liquid through a connection fitting with a cannula attachment pipe to a cannula; compressing means to regulate the stream of said liquid through hose by means of a mechanism for multiple predetermined dosing; a suction source connected to a suction cup, triggering means corresponding to firm skin contact of the suction cup for operating said dosing compressing means and means for blocking and marking said blocking of the function of said injector, if the liquid supply into said container with hose is nearly exhausted.

More specifically, the invention is embodied in a device which is described as follows. A liquid container of a suction injector has a pressurized gas filled compartment sealed by a membrane and a hose, which leads through a kind of roller pump, driven by a spiral spring, which is reset by applying pressure to an axis rod with a spiral groove in which a follower from a disc locks. The blocking effect of the dosing pegs, screwed in holes in said disc by a shiftable bolt, is removed by the beveled edge of said shiftable bolt. The suction is caused in a case replacable for single use, consisting of an outer chamber with factory-produced stored under-pressure in an inner portion, which expands downward to the suction cup towards said attachment pipe provided with a covering lid with funnel which is continued in a cannula shaft moulded in said covering lid. A supporting tube around the cannula is lifted by the skin, thereby a hole is opened between the outer chamber with stored vacuum and the inner portion, which was closed by the supporting tube, so that the skin is sucked into said suction cup and works through a tube and a hose connection to a little folded bellows, whose contaction effects by a spring-loaded mechanism a brief retraction of said shiftable bolt causes, that the blocked dosing pipe is frozen together with freezing of the movement of said disc whose springing blades, pressing said hose against a groove inside of a plug-in-unit, transports said liquid through the cannula under the skin until the next dosing peg in the row of the inserted dosing pegs is blocked by the sharp edge of the shiftable bolt. At the same time a valve stem with tapered hat is pushed backwards by said blocking dosing peg. Delayed by a nozzle, the valve opens the suction cup to the outer air and the skin retracts from the cannula. If the liquid supply is emptied, a spring-balanced taster finger moves along with a loop of the hose and triggers a swivel arm, driven by a spiral spring, which touches the skin and catches at the rim of the suction cup, to hinder a continuation of use. A revolution counter allows a control of the volume.

It will be understood that each of the elements described above, or two or more together, may also find a useful application in other types of suction injectors differing from the types described above. Although the examples are limited to the use of positive displacement pumps using mobile means of sealing along the tube, the technically already familar solution of dosing from hoses or tubes, using a measurement of the fluid flow in connection with a tube-cross-section-throttling, using electronic calculating and steering means, should not reduce the idea (spirit) of the invention, which is presented here.

BRIEF DESCRIPTION OF THE DRAWINGS

FIG. 2 is a cross-sectional side view of an example similar to that of FIG. 1.

FIG. 5 is a sectional view taken along line A-B of FIG. 4 showing the steering means of the example of FIG. 4.

FIG. 6 is a view along the arrow C of FIG. 5.

FIG. 7 is a view along the arrow D of FIG. 5.

DETAILED DESCRIPTION OF THE PREFERRED EMBODIMENTS

Figure 1:
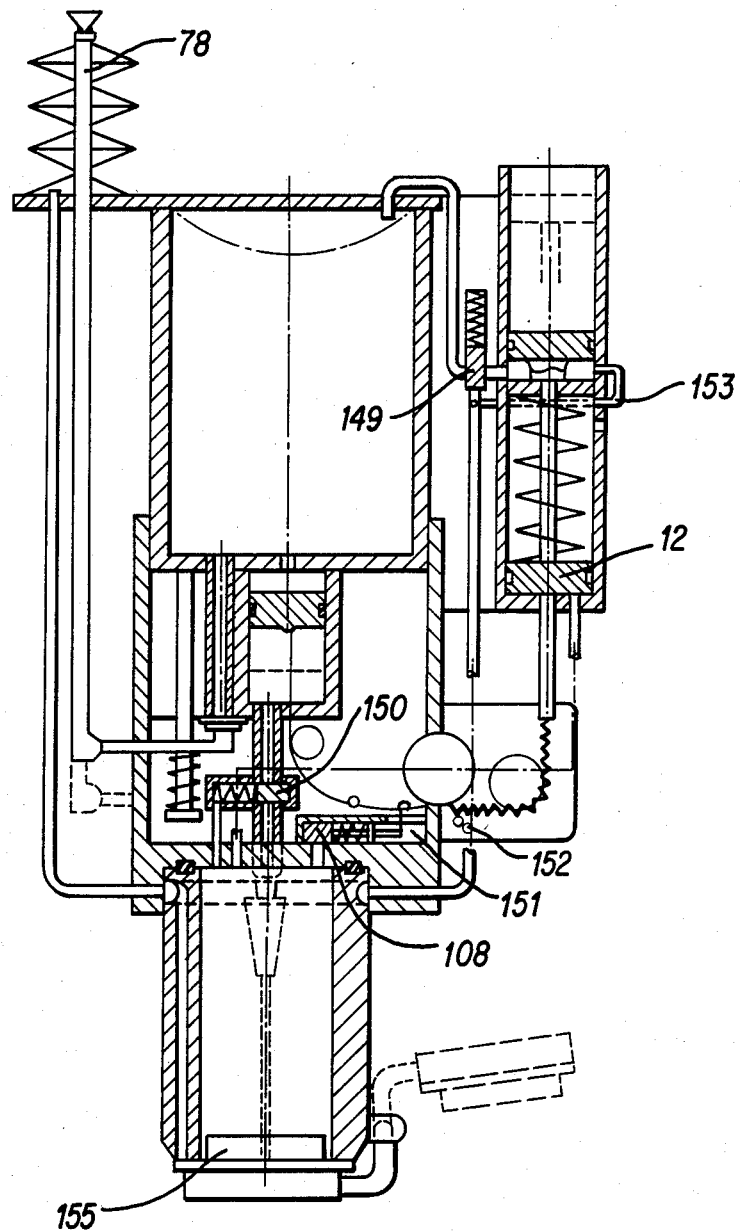
FIG. 1 shows in a cross-sectional side view an example of the invention, in which the suction is brought about by a piston driven from the pressurized gas inside of the medicament pressure bottle with a lid sealing the tip of used cannula in a cushion.

FIG. 1 shows a disposable device as a whole in which the medicine outlet from the pressure bottle into the dose chamber is briefly opened by pressure on the triggering plate by means of the lever (78), which is connected to the plate, at first through the spring attached to valve-hinge, so that the dose piston is lifted a distance, which the binding ring (151), movable for dosing along steering markings and shortening the string, permits. The folded bellows is then pressed together, and if the opening (81) in the suction cup rim is closed (by skin) the displace piston activates the valve (85) letting in the gas from the pressure bottle under the propulsion piston (128). By means of the piston rod, the propulsion piston pushes the suction piston, which causes the sucking on of the skin through the channel (7) and the tightening of the spring (103) on the spring. If the valve (150) is opened by suction, the medicine is emptied out through the cannula, when the string is pulled by spring. Finally a knot in the string affects the outlet-valve (108) of the suction area. The spring (154) leads the suction piston back. After use the cannula point is sealed with disinfecting plate on the lid (155). The suction shell (156) is removed for new use, thus the cannula can be changed.

FIG. 2 shows a variation with a centrally attached triggering button (78) and rod. The pressurized storage bottle is turned as a whole, while the valve plate is fixed on a cone in a slide of the wall, so that one dose chamber after another is filled to the extent permitted by the proper lengths of cord. The triggering rod causes the opening of the valve (85) against the spring after delay by a snap catch. The gas flow activates the propulsion piston (128) and thus the spring attached suction piston, which causes the sucking on of the skin. Further lowering of the triggering rod frees the gas tube (130) to the dose chamber, while the check valve for the air exit is closed by pressure. The valve (150), which is kept closed by a spring, is then opened, so that the medicine can flow out. Finally, the movement of the suction piston causes the opening of the outlet-valve (108), while a little quantity of air enters through the seal of the suction piston rod.

Figure 3:
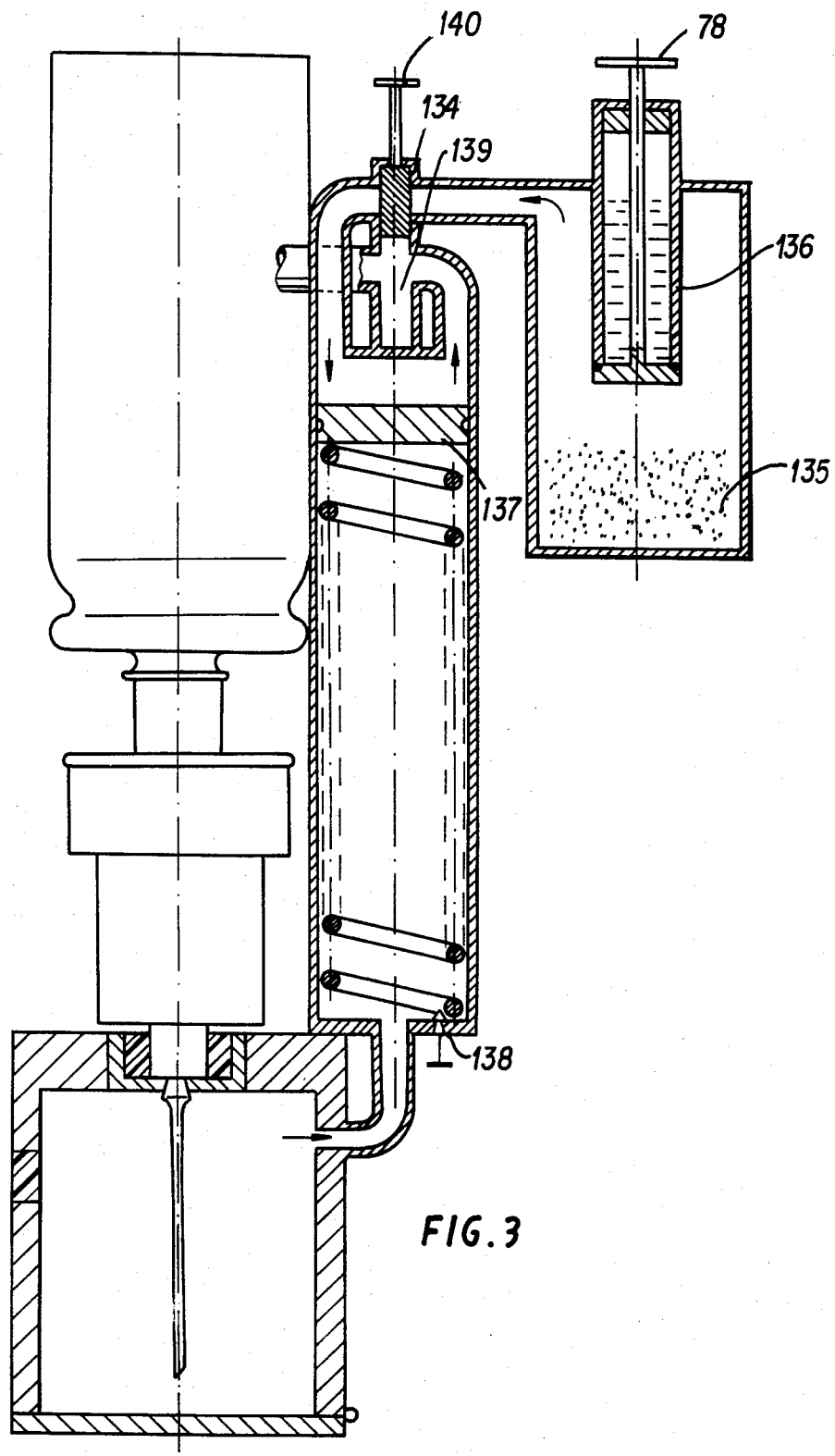
FIG. 3 shows in a cross-sectional side view an example with a gas producing mechanism.

In variation A (FIG. 3), the piston is moved by gas pressure, which is created by the mixture of gas producing substances, with or without detonation for an explosion, in the technically known manner. FIG. 3 has a medicament pressure bottle (36) with a dosing hat-piece (133) sticking air-tightly in the suction cup (4), the valve (134) and the case (135) with gas producing powder with the cylinder (136) closed by a valve disc with stem (78) and a suction producing tubular cylinder (137) with a spring-driven piston and with check valve (138). If the stem is pushed downwards, the liquid flows out into the powder and produces gas pressure. If the valve (134), now shown closed, is opened, closing the outlet valve (139), the piston is lowered against the spring pressure while the check valve closes. The lid of the suction cup may be opened and the cup is put on the skin. If the valve-rod (140) is withdrawn, the piston moves upwards driven by spring while the check valve opens and causes suction in the suction cup.

Figure 4:
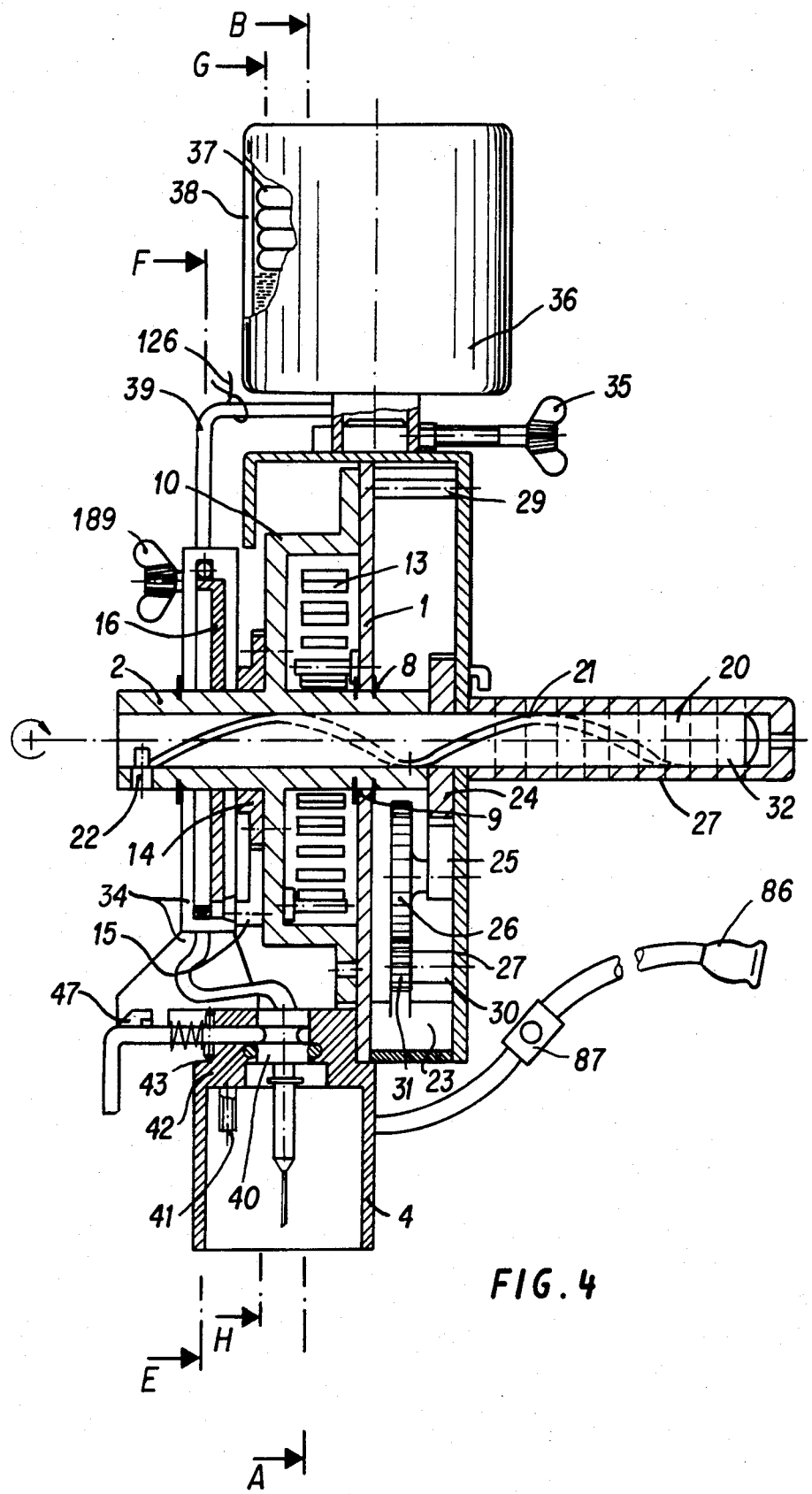
FIG. 4 shows in a cross-sectional side view the prefered example with a hose pump demonstrating also the medicament pressure bottle and a suction cup for use by an outside suction source.

The device in FIG. 4, shown in sectional side view, consists of the housing shell (1), in the center of which the bush (2) is inserted, a pushing of the bushing against the bottom of the housing being prevented by two clamp rings (8, 9). The disc (10) is firmly connected with the bush (2). Between the bottom of the housing and the disc (10) lies the spiral spring (13), the one end bolt of which is attached to the bottom of the housing, while the other is attached to the disc (10). On and attached to the disc (10), there is the ratched wheel (14), the pawl (15) of which, under light spring pressure, is attached to the dosing wheel (16), which has the spring blades (18) on the cambering ring (17) and is turnable around the bush (2) and secured by the clamp ring (19) against being lifted from said bush. The axis rod (20) is movable and positioned inside of the bush (2). The follower (22) locks to the spiral groove (21) through the bush. For the use of the revolution counter (23), the ratched wheel (24) has its own axis. The pawl (25) is connected to the gear wheel (26), which turns freely around the bush of the ratched wheel (24). Between the covering plate (27) and the bottom of the housing, there are the attaching screws (29) and the axis (30) of the gear wheel (31), which drives the revolution counter (23). The toothed wheel (31) is in gear with the gear wheel (26) in a transmission relationship of 3:1. On that part of the axis rod (20), which is visible above the covering plate (27), there are ring-shaped markings (32), spaced equidistantly, with numeral designations for the daily medicinal dosage. The end of the axis rod (20) which sticks out is rounded. The covering case (33), which prevents accidental activation of the axis rod (20), is connected with the covering plate (27) by a bayonet cap catch. A plug-in-unit (34), which is removable from the housing shell (1) and is made of transparent plastic, for example acetate-plastic, carries the fixing bracket (35) for the medicine pressure bottle (36) with the filled folding bellows (37) (filled with gas and closed by the membrane on the upper and lower ends and attached to the top end of the bottle), and the drainage grooves (38), which bring about an emptying of the folds. A tube (39) leads from the medicine pressure bottle within a half-moon-shaped groove in the plug-in-unit (34) through the connection fitting (41) with the cannula attachment pipe to the suction cup (4). The tube (41) is sealed against the suction cup and leads into it. The suction cup rests with its cylindrically narrowed upper end (42) in the boring (43) of the plug-in-unit (34). Three plastic bars (44) on bias springs lead from an annular rim strip of the boring (43) through the slit in said cylindrically narrowed upper end (42) of the suction cup into the annular groove of the connection fitting (40), which is sealed to the suction cup under the slit by a sealing ring (45). A second annular rim strip (46) serves as a stop for the claw (47) of the plastic bar. The connection fitting (40) has an eccentric boring for the insertion and sealing of the tube (41).

The cross-section of the FIG. 5 in the level A–B of FIG. 4 goes through the interior of the spiral spring (13) and then, in their middle thirds, the screwing holes of the disc (10) of the screwed-in dosing peg (48). The holes are in a concentric row. Then the cross-section goes through the slit (62) of the steering gib (51). It can be seen, that a tube (41) leads at an angle into the small folding bellows (50), which is in a boring and belongs to the sterring gib (51). The tube (49) is connected to its attaching case (52) by a pressing piece. The closed and movable other end of the bellows continues into the shifting rod (53), the boring of which crosses crosswise the boring of the peg (54), which goes through the open slit (55) at the end of the lever (56) and then has a screwed joint with the washer (57) over the rear of the lever. A counternut lies under the slit. A bias spring (58) is attached under the one arm of the lever (56), The end of the other arm of the lever effects a kind of trip cam (59), which begins with a shoulder and ends rounded. The trip cam is attached to the shiftable bolt (60), which springs back because of spring pressure. The flat surface of the end of the dosing wheel, limits the movement of the dosing wheel, while in the opposite direction (counterclockwise) a beveled surface causes a release of the dosing bar (60). The turning axis (61) of the lever (56) goes diagonally through the slit (62) of the steering gib (51) and rests within a slot (63) of the lever (56), which supports itself by means of the pressure spring (64) against the turning axis and tends to move in the direction of the shiftable bolt (60). The cocking lever (65) is swung out of the slit of the steering gib (51) around the turning axis by means of the spiral spring (66). Right before the shift, bolt (60) one sees the valve stem (67) with a tapered top on springs which is pushed back from the dosing rod. This movement causes an opening of the valve, which leads into the canal (68) through the adjustable nozzle (69) to the folding bellows (50) and to the tube (41), connecting this to the ventilation opening (70). One also sees the tracer finger (72), which is attached to a hose loop (71) and has spring suspension towards the hose loop. Over the rounded end of the tracing finger, there is the anchoring lug of a swivel arm (73), which pushes downwards along the cross-axis (74) by means of a spring.

The view of FIG. 6 along the arrow C of FIG. 5 gives a view along the axis of the dosing peg (60), which demonstrates, that the latter rests against the upper part of the dosing peg (48) with its end surface touching the wedge face and thus blocks the movement of the disc and so also of the dosing wheel in a clockwise direction. The dosing peg has above the wedge face a rectangular beam, which moves to the left until it touches the blocking rod (80), which is fastened in the next screw hole to the left on the disc. The blocking peg (80) is irremovably screwed under the disc and limits the turning of the disc in both directions, in the illustrated case movement in a counterclockwise direction.

In FIG. 7 the view along the arrow D in FIG. 5 also shows the swivel arm (73) and the position of cross-strut on the tracing finger (72). The position of the valve (67) with its tapered top in the free space under and pushed somewhat to the right of the dose bar (60) is made clear.

Figure 8:
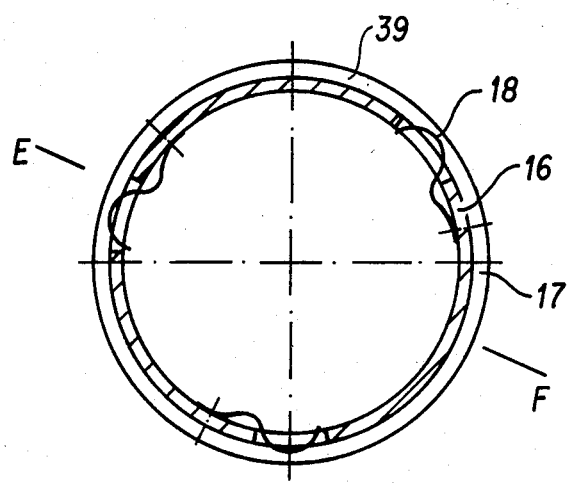
FIG. 8 is a cross-section taken along line E-F of FIG. 4 showing a ratched wheel with pawl.

Along the line E–F of FIG. 4 in FIG. 8 the dose wheel is shown with three spring blades (18), which, moving inwards in a wide arc, press the tube (39) together and thus regulate the flow.

Figure 9:
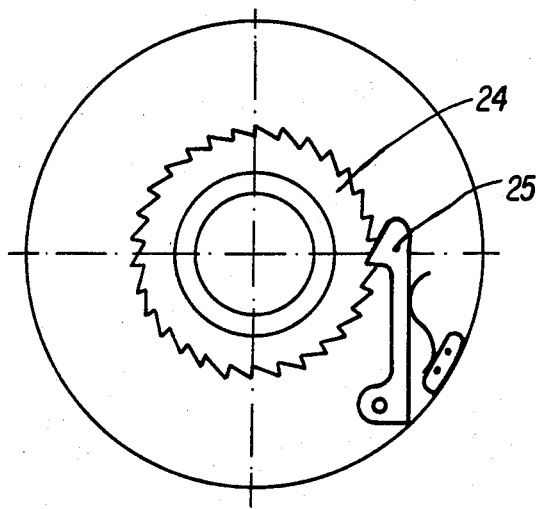
FIG. 9 is a cross-section along line G-H of FIG. 4 showing the spring blades of the dosing wheel.

FIG. 9 shows a cross-section on level G–H of FIG. 4 and shows a ratched wheel (24) and its pawl (25).

Figure 10:
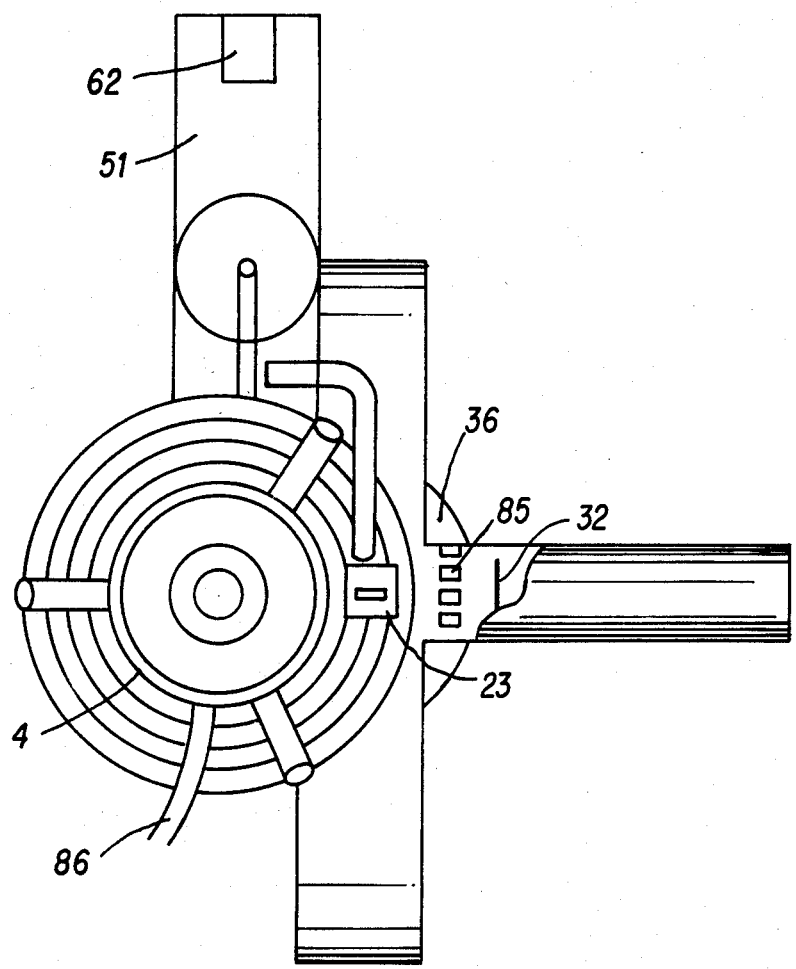
FIG. 10 is a view along arrow I from below of FIG. 4.

In FIG. 10 along the arrow I of FIG. 4 a view is shown of the suction cup from below to the slit (62) of the steering gib (51) and through the lens-like windows (85) of the transparent-plastic covering case (33) the ring-shaped markings (32) of the amount of the dose of medicine. The arrangement of the revolution counter (23) and of the suction tube (86) is clearly shown. The contures of the medicine pressure bottle (36) which is positioned above, are shown. The covering lid (188) for the suction cup (4) with the rubberlike sealing cushions (155) for sealing used cannulas has been removed (see FIG. 1).

In order to make the device ready for use, first, the wing nuts of the holding clamp (35) are released, then the screwed joint (89) between the housing shell (1) and the plug-in-joint (34) and, finally, the plastic bars (44) on springs are drawn out of the upper part (42) of the suction cup (4) and are fixed, one after the other, with their respective backwards claws (47) on the projecting outer edge of the rim strip (46). If a used medicine pressure bottle is present, it can be pulled out with hose and connection fitting and, if desired, replaced in any given order. Care must be taken, when the hose (39) is inserted into the half-moon-shaped groove by means of the rim strip of the dosing wheel, and the plug-in-unit approaches the housing shell, that the hose loop (71), which is best produced by a kind of rubber band connection, sticks out of the attachment and now comes into the predetermined recess in the steering gib, for which purpose the tracer finger (72) must be pulled back. The screwed joint (189) is now closed. The programming of the dose is done by means of a keyrod. As a rule, once at the beginning of every day, the covering case (33) is removed from the axis rod (20), and its end is pushed into a lower position, so that it twists itself down into the bush (2). At the same time, the disc (10) turns under the influence of the follower (22), while the spiral spring (13) is made tense in a clockwise direction, and while the shiftable bolt (60) is pulled back to the wedge face (91) under the influence of the passing dosing pegs until the turning movement is stopped, when the shiftable bolt strikes the beam of the blocking peg (80). If a new medicine pressure bottle is being used, its hose clip (126) will be opened and removed, so that medicine flows into the hose (39) up to the next spring blade (18) of the dose wheel (16). When the shiftable bolt is pulled back on the loop (127), this causes under the influence of the spiral spring (13) a clockwise turning of the dose wheel, until the blocking rod (80) strikes the beam of the shiftable bolt. The tightening of the spiral spring by pressure against the axis rod and the releasing of the shiftable bolt by pressure against the loop are repeated, until the medicine exits from the end of the connection fitting. The swivel arm (73) is raised against its sprial spring, until its anchoring lug comes past the end of the valve (67), which is springing back to rest on said valve.

The swivel arm (73) is thus prevented from striking back down again to the suction cup. If the medicine supply in the tube has been used up however, then the tube loop collapses and offers no more resistance to the tracer finger (72), so that its pressure spring pushes in the same direction as the anchoring lug of the swivel arm (73), which presses against the rounded end of the tracer finger, thus causing the swivel arm to give warning by snapping down. Before every injection, the cocking lever (65) must be turned in such a manner around its axis, that it can be pressed into the slit (62) of the steering gib (51), by which action it presses against the lever, the end of which springs back in the slot (63) for the axis (61) past the trip cam (59) of the shiftable bolt and comes to rest on the shoulder-surface of the shiftable bolt (as shown in FIG. 5). This position of the lever (56) is maintained, becuases its peg (54) comes to rest on the shifting rod (53). The small folding bellows (50), which acts as a spring, was now able to spread out after the withdrawal of the peg (54). If the suction cup is now pressed against the skin, and if a strong suction works through the mouthpiece on the suction tube (86), the skin is then sucked into the suction cup (4) and onto the cannula (28), which is attached to the connecting fitting, and the underpressure is maintained, because the check valve (87) is closed. The underpressure works on the folding bellows (50) through the tube (41) and the tube (49), so that the folding bellows collapses. The withdrawal of the shifting rod (53) causes the penetration of the peg (54) and the movement of the lever (56) corresponding to the effect of the leaf spring (64). Thus the end of the lever meets to surface of the switch cam of the shiftable bolt (60), so that this is briefly drawn out, by which action the blocking effect of the adjacent blocking dosing peg is cancelled, and the dosing wheel (16) is put into rotation with the help of the spiral spring (13). The spring blades (18) are also moved along the hose (39) and push the predetermined amount of medicine under the skin. In the stopped position of the shiftable bolt (60), which is shown in FIG. 7, the valve stem (67) was pushed back on its tapered top from the dosing rod, on which it was resting. Because the air supply to the suction cup has been cut off by means of the nozzle (69), the vacuum could be maintained there, until the dosing wheel turned, allowing the valve stem (67) to come down from the dosing peg with its tapered top and to come into a stretched out position with the assistance of its bias spring, so that the reventilation valve closes, until the following dose rod comes to rest on the dose bar causing the valve to be again activated.

Figure 11:
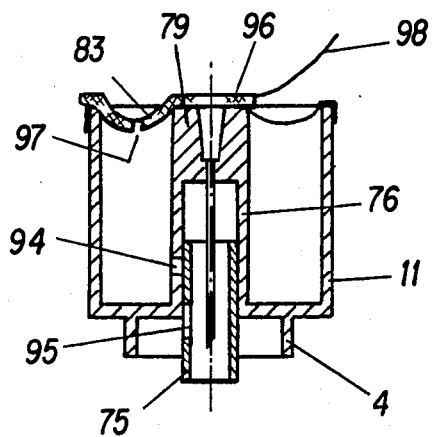
FIG. 11 is a cross-sectional side view of a suction storing suction cup for use with the hose pump.

FIG. 11 shows the device, as it looks, after it has been removed from packaging before use. It consists of an outer chamber (11) with a central conical opening (79), which continues downwards into the firmly held cannula shaft. An inner portion (76), which expands downwards into the suction cup (4), surrounds the greater part of the cannula shaft. A supporting tube (75) slides into the inner portion (76) and extends beyond the rim of the suction cup (4). A lateral cross-groove (95) of the supporting tube (75) lies under a lateral boring (94) of the inner portion. An adhesive mass seals the space between said lateral boring and the wall of the inner portion. The membrane (38) is drawn in inside of the inner portion by vacuum in a ring-shaped manner and is covered by a strip of a membrane (96) which is adhesive on its lower side, in such a manner, that this strip of the membrane covers and seals a hole in the membrane (83) and the central conical opening (79) serving as a funnel. The membrane (96) continues into the free end (98).

Figure 12:
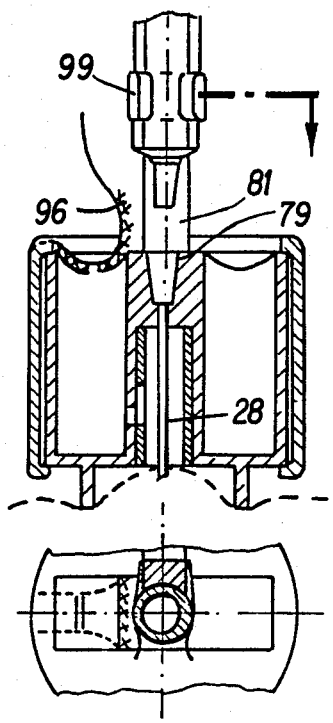
FIG. 12 shows a device as in FIG. 11 in use.

FIG. 12 shows a device as in FIG. 11 on which a syringe-holding groove (81) with the clip ends (99) and the headpiece, which is partially open, is so positioned, that an injection syringe, ready for use, comes to rest between the clip ends (99) with its cone over the conical opening (79). The supporting tube was lifted by pressure against the skin, which is indicated by the dotted line, so that the slanting slit of the supporting tube comes into position over the hole of the inner portion. An equalization of pressure between the suction cup and the inner portion, which originally had underpressure, is thus brought about, causing the skin to be raised, so that it is sucked tightly onto the rims of the suction cup and penetrates the point of the cannula shaft. The membrane (96) is pulled by its end (98) so far to the left, that the central conical opening is exposed. For the continuation of use, the syringe must be pushed downwards in the direction of the arrows within the clip ends, until the syringe cone lies firmly and air-tightly within the central conical opening. The injection is brought about in the standard manner by pressure on the syringe piston, which is not shown. An additional pull on the end (98) of the membrane (96) frees the hole (97) of the membrane (83), so that exterior air can flow through the inner portion (11) into the suction cup area. The skin thus drops back and releases itself from the point of the cannula and from the rim of the suction cup. The membrane strip (96) in a simplified variation, does not extend over the central conical opening. In this case, the syringe is already connected tightly to the device by means of the syringe cone inside the central conical opening, before the device is placed on the skin. A precondition for this is a certain amount of friction force between the syringe piston and cylinder, which prevents a movement of the piston and the influence of suction from the suction cup in the time before penetration of the cannula point into the skin. A support piece between the syringe piston and syringe cylinder, which is removed immediately before the emptying of the syringe, can also serve this purpose. The device can also be connected with the conical pipe of a medicine dosing device, as shown particularly clearly in FIG. 12 of U.S. Pat. No. 4,139,008 (of Feb. 13, 1979) or in FIGS. 4 to 10 of the above described device. A partial view can be seen in a detail of FIG. 2, shown from above.

Figure 13:
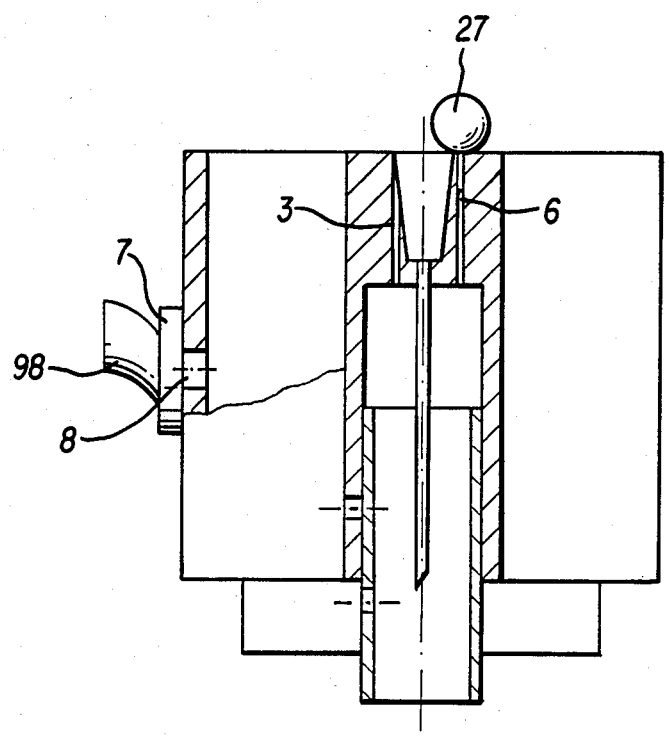
FIG. 13 shows a cross-sectional side view of a device as in FIG. 11, schematically simplified and at a ratio of 2:1 which shows details of the regulation and a coupling means to an injector as described in FIGS. 4–10.

FIG. 13 shows a cross-sectional side view enlarged in a ratio of 2:1, a device as in FIG. 1. In addition, a boring (3) to the inner portion has been put into the central opening. No air can escape from this boring, as long as the syringe cone is sealed to the device. If this syringe cone is lifted after injection, the reventilation occurs. An additional channel (6) is useful, when a medicine dosing device is used, which is especially designed to give the predetermined dose of medicine when triggered by an impulse of negative pressure. For such usage, a reventilation boring (8) in the outer chamber can be of use as part of an automatic injector, when a role of adhesive tape, which seals the boring, is pulled back after the injection, so that air can enter through the reventilation boring. A cannula with an air-tightly sealed rubber sack is placed in FIG. 11 into the channel (6). The sack was pushed by the syringe cone somewhat to the side, but it indicates by collapsing the influence of vacuum in the inner portion. Polystyrene with little gas permeability is, for example, suitable as a material for the production of the device for suction injection.

Figure 14:
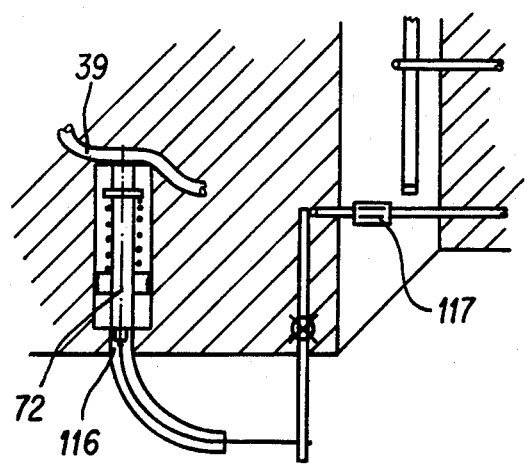
FIG. 14 shows schematically in cross-section a blocking mechanism as similarily seen in FIGS. 5–7.

FIG. 14 shows a variation of the protective mechanism against use of the device after exhaustion of the medicine supply. The tracing finger (72) is, as in FIG. 5 directed against a hose (39). In its extension, the end of a Bowden cable (116) is positioned, which activates a lever (56), the other end of which (after the effect of tension resulting from the reduction of liquid pressure in the hose loop) brings a blocking gear (117), which is positioned and secured against rotating on a square axis, into mesh with a gear of the revolution counter. The function of dosing is thus also blocked.

Figure 15:
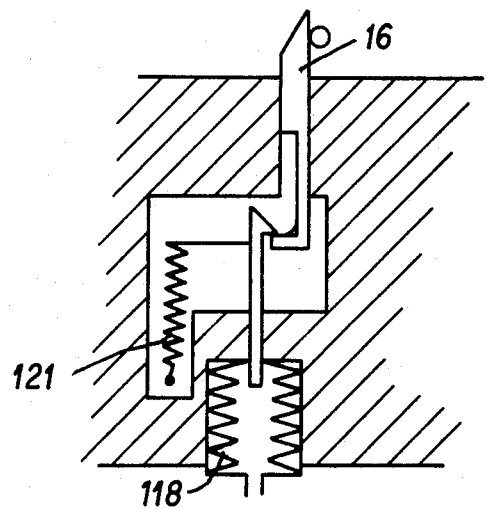
FIG. 15 is a cross-section detail of an alternative arrangement for the shiftable bolt as described in FIGS. 4–10.

FIG. 15 shows a variation of the activation of the shiftable bolt (60) by means of a folding bellows (118). The shiftable bolt is extended into an elastic tongue with a cross-cam, into which the cross-cam of the magnet anchor, which can be brought back by means of the spring (121), grips.

Figure 16:
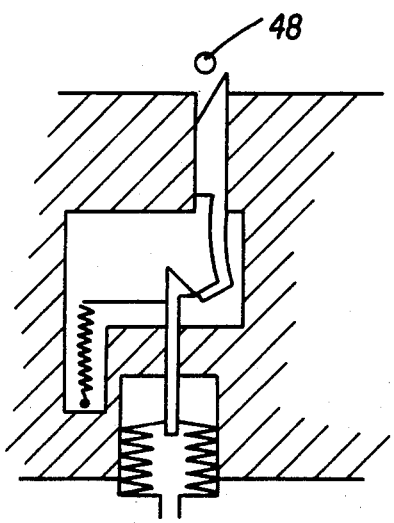
FIG. 16 is a cross-section of the device of FIG. 15 in function.

FIG. 16 shows the same arrangement at the moment of activation of the folded bellows. The shiftable bolt has already been drawn back far enough for the dose peg (48), which was blocked by it, to move by. Since the elastic tongue on the shiftable bolt moves away from the support in the housing, it also moves away from the cross-cam of the folded bellows, so that this cam moves past the cross-cam of the dose bar. During the returning movement, the wedge face on the cross-cam of the magnet permits a new hooking in behind the cross-cam of the dose bar in spite of the limited elasticity of the latter during the evading movement.

Figure 17:
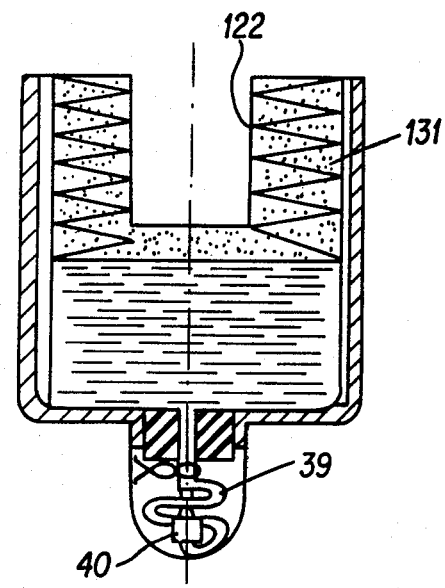
FIG. 17 shows in a cross-sectional side view a schematical medicament pressure bottle arrangement.

FIG. 17 shows a schematically simplified cross-sectional side-view of a medicine pressure bottle, the upper wall limitation of which is drawn in a so key-like manner into the folding bellows (131), that there is room in the key hole (122) for the bottle neck together with the hose (39) which is wrapped around the connection fitting (40). A hose clip (124) prevents medicine from entering into the tube. A longitudinally inserted channel with a side open to the folding bellows facilitates the flow of liquid out of the folds of the folding bellows. Such a channel in the right wall is depicted as a depression in the bottle.

Figure 18:
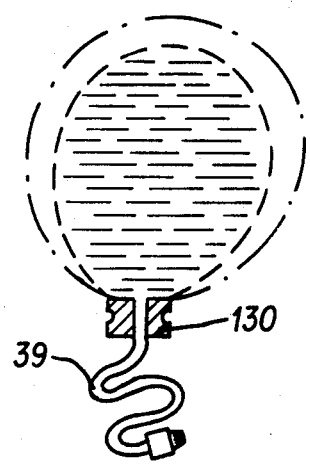
FIG. 18 is a cross-sectional side view of a bag as a liquid container, schematically presented.

FIG. 18 shows in lateral cross-section a variation of the container, consisting of a less elastic outer container which is filled with pressurized gas. Within it, there is a further membranous container with liquid, which empties solely into the hose (39), which is surrounded and sealed by an attaching plate (132).

Figure 19:
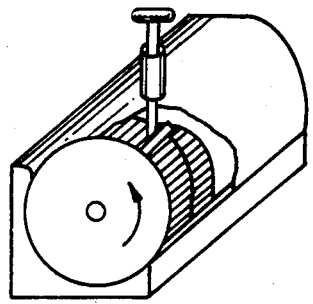
FIG. 19 is an enlarged-scale view of a top plan detail view of a blocking mechanism.

FIG. 19 shows in sectional side view the gear of a revolution counter with a striking cam, which is blocked by a rod in a predetermined stage of the revolution.

Figure 20:
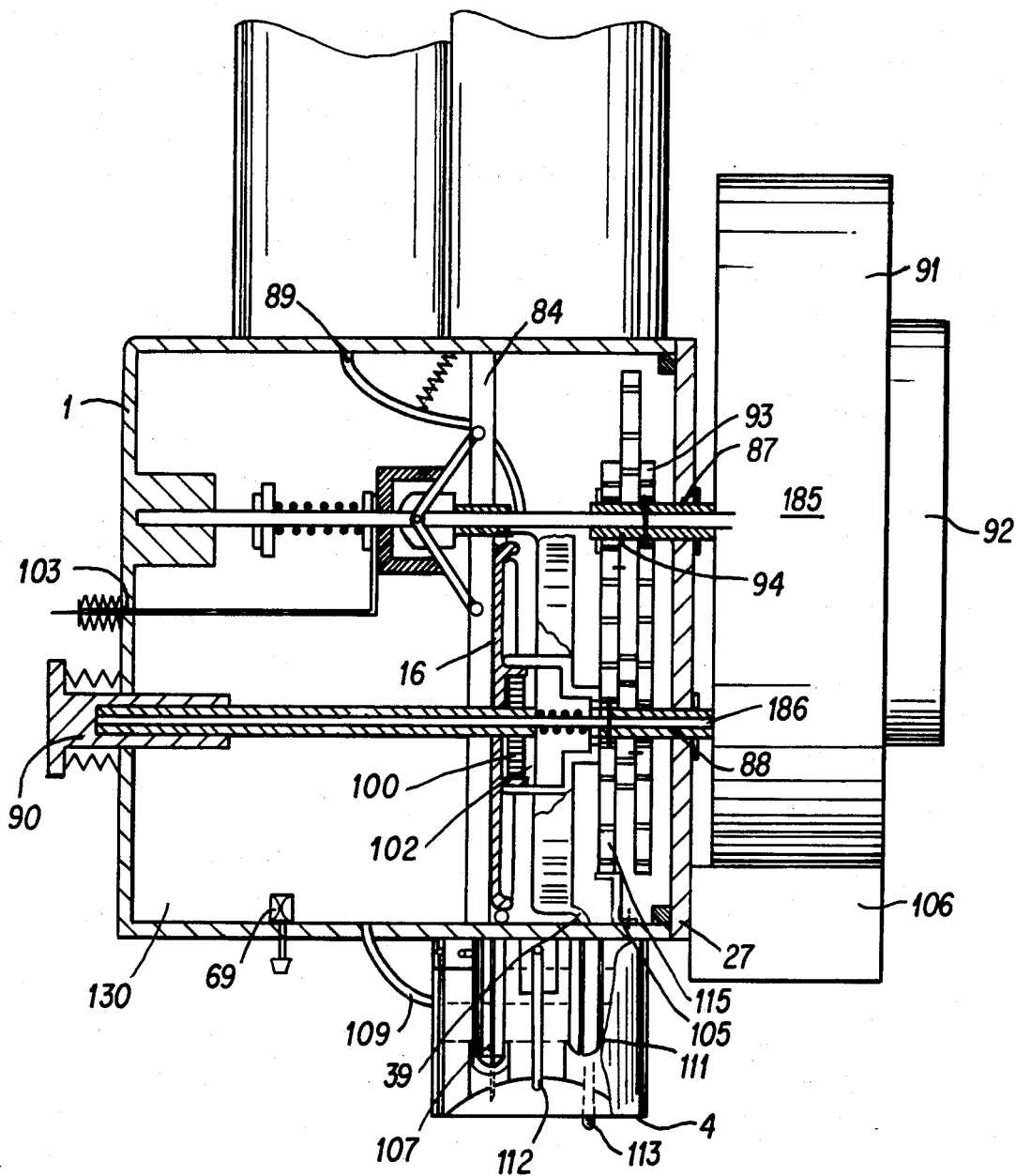
FIG. 20 is a schematical cross-sectional side view of an electrically driven device.

FIG. 20 shows in schematic form an example using electric propulsion and electronic steering. The construction of the apparatus is to be understood as follows.

Between the covering plate (27) and the cross-beam (84) of the housing (1), there are the square shafts (185, 186) in their bushings (87, 88, 89, 90). The square shaft which is generally secured against falling out by clamp rings, is connected to the driving shaft of an electric motor (91), and this driving shaft is connected to a compressor (92). The first gear wheel (93) rests on the square shaft (85) and is carried along by it. The other gear wheels run on the bushings (94, 88), except for the last gear wheel, which is connected to the square shaft (86) and transfers in a retarded manner the revolutions to the dosing wheels (16, 95). This is done by means of a pinion (100), which is movable along the square shaft, and which is enmeshed in a bushing (102) with inner teeth by means of a plunger case (90), which simultaneously serves as a rest in the housing wall. The pinion is at this point fixed in this position by a detent pawl (101) which is engaged in a ring groove. The bushing (102) is firmly connected to the dosing wheel (16), which causes the dosing in the hose (39) to the corresponding cannula attachment pipe. A positioning of the pinion is shown, in which it is brought by means of tension on the plunger case under the influence of its bias spring. The pinion grips into the bushing with inner teeth of the dosing wheel (95) and transfers the dosing turning movement to the wheel and transfers the medicine through the corresponding tube to the other canula attachment cone within the suction cup (4). The centrifugal force regulator, the weight burdened swivel arms of which are pulled back by tension on the starting lever (103) from the prop of the cross beam (84), starts to function under the influence of the motor by means of the simultaneously activated electrical switch contact, driven by means of the square shaft (85). At the same time, the bushing, which is hollowed out in a pot-like manner, is movable along the wing arms of the square shaft and surrounds the attaching heads of the wing arms, is pushed to the left against its adjustable spring. This spring mechanism causes, shortly after the number of revolutions of the motor has been reduced by the turning off of the motor, a blocking of the rotation of the wing arms on the housing prop. The dosing occurs with control counting by the switch cam (105) by means of the electronic control unit (106). The sealed housing is connected to the suction cup by the channel (109) and has a reventilation nozzle (69). The starting lever (103) and the plunger case (90) are sealed to the housing by the folding bellows. There are contact rods (107, 111) with connected springs next to the two cannula attachment cones. A further contact rod (112) is positioned between the cannula attachment cones and is activated by the skin which has been drawn up by vacuum. It can also be replaced by an extension tube, which continues into the hose (86) to the compressor and can serve as a sensor switch (129). Three contact rods (113) for starting the motor are near the suction cup rim. The starting button is activated by a pull on the starting lever (103) as a contact on the housing wall. The choice of programming takes place by means of contacts, which are activated by means of the end positions of the plunger case (90). The batteries (130) are positioned in a special housing part. The electronic control unit (106) is next to the motor.

Figure 21B:
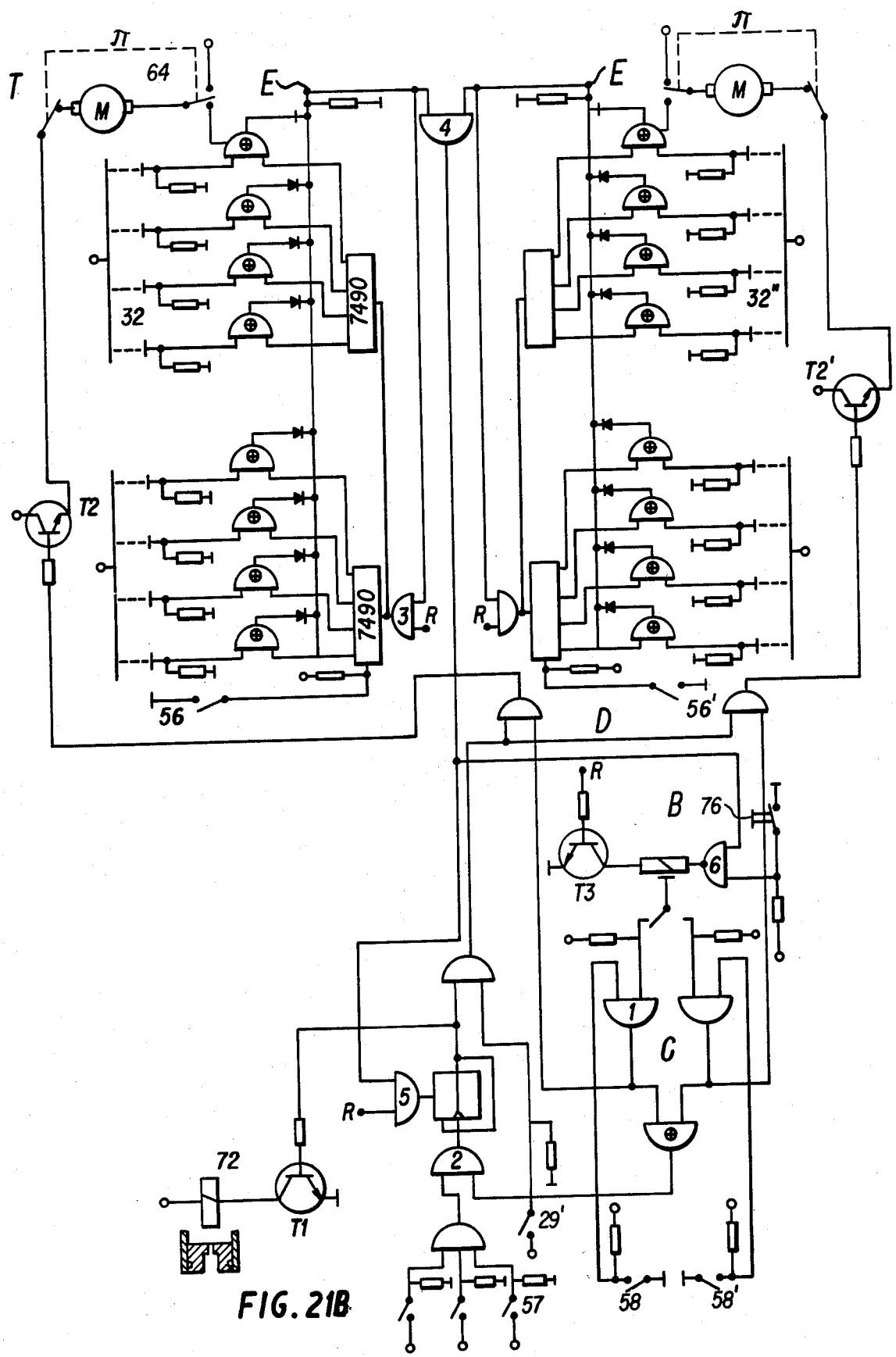
FIG. 21 gives a wiring diagram of the device in FIG. 20.

FIG. 21 shows a simplified electronic wiring diagram for this. The given voltage should be on the contact points which are designated 5 V, and the voltage of the gate-reset on the points designated R. Individual wiring and diodes have been left out for the sake of simplicity and lucidity. After the switch for choice of program has been set for the dosing, the hand activation of the switch-reset causes a slow build-up of voltage 5 V on a condensor, in order to bring the switch into the zero-position. The bistable relays of B are for programs I or II and can be manually switched by the program switch button. The pressure contact (107) or (111) is closed by the placing of the cannula on the cannula attachment cone and, in part C, compared for correspondence by means of the two AND-gate (1) TTL SN 7408 and the EXOR-gate TTL SN 7486. The circuit leads from there to the AND-gate (2) TTL SN 7408, which breaks the circuit to the compressor (92). If the AND-gate on the suction cylinder is closed three times (by positioning on the skin), then the flip-flop switch TT1 SN 7474 turns the sucking compressor on by means of the Transitor T(1). Now underpressure is created in the suction cup by means of the hose (39). The skin is lifted in the suction cup and thus activates the contact rod and thus switches the NAND-gate TTL SN 7400 from the position low to the position high. In part D of the dosing program, the pace motor for the dosing wheel (16) is switched from low to high by means of the NOR-switch TTL NN 7402 through, depending on the position of the bistable relay, transistor (2) or transistor (2'), when the bistable relay and the compressor have been turned on. The trigger cam contact (105) is activated by every revolution of the gear (115) and leads into the decimal counter TTL SN 7490. The comparison of the counter with the preselection switch occurs by means of a EXOR-gate TTL SN 7486 with correspondingly arranged diodes IN 4148, until the flow of current has been switched at point E from high to low. The counter is set at the zero-position by low at E by means of the AND-gate (4), but the flip-flop switch is flipped into rest position by means of AND-gate (5), and the bistable relay is flipped into the other position by means of NAND-switch (6). The transistor (3) and the switch-reset insure, that the bistable relay does not change its switch position because of the turning on and off of the device.

I claim:

1. A suction injector, particularly for use with hypodermic injections, comprising a liquid container with a pressurized gas compartment sealed from said liquid; a hose connected to said liquid liquid container for the transmission of said liquid through a connection fitting with a cannula attachment pipe to a cannula; compressing means moved by a motor which is in connection with a power source, to regulate the stream of said liquid through said hose by means of a mechanism for multiple predetermined dosing; a suction source connected to a suction cup; triggering means corresponding to firm skin contact of the suction cup for operating said dosing compressing means; and means for blocking and marking said blocking of the function of said injector, if the liquid supply into said container with hose is nearly exhausted.

2. A suction injector as defined in claim 1, wherein a hose pump serves as means to regulate the stream of said liquid through said hose; by using a disk provided with holes in regular distances for inserting of pegs blocked by a shiftable bolt as mechanism for multiple predetermined dosing; wherein said bolt has a beveled edge which is pulled backward during the passage of one of said pegs when they are moved in the direction opposed to the movement of the pressing means of said hose pump; said shiftable bolt having erected edges opposed to a longer peg for blocking the movement of said disk; said shiftable bolt being pulled backward by a spring mechanism with over taking cam; wherein said spring mechanism is triggered by a bar operated by suction; said operating means of said bar being a folded bellows, which is in a tubular connection with said suction cup, which for his part is in connection with said suction source; a spiral spring serving as said motor to turn a disk connected with a wheel by a ratched wheel with pawl; a ventilation stem being pulled back by said peg, if it is blocked by said shiftable bolt opening a valve for reventilation of said suction cup; being a taster finger as blocking and warning mechanism, one end of which is positioned on said hose, while the other end functions as said means for blocking the functioning of the device, if said hose collapses, in the case that said liquid is nearly exhausted.

3. A suction injector as defined in claim 1, wherein said part of said hose, in which said end of said taster finger is inserted for blocking the liquid stream, has a loop.

4. A suction injector as defined in claim 1, wherein said other end of said taster finger blocks the movement of a swivel arm, which touches the skin and catches at the rim of said suction cup.

5. A suction injector as defined in claim 1, wherein a plug-in-unit has a bracket for the fastening of said liquid container and a holding ring for said suction cup and means for being connected to a housing.

6. A suction injector as defined in claim 1, wherein the compressing means of said hose pump are blad springs fitted to parts of a wheel in a plurality and moved along said hose positioned in a cambering producing counter-pressure.

7. A suction injector as defined in claim 1, wherein said spiral spring is made tense by an axis rod, into the cam slot of which a cam follower is inserted to turn said disk connected with said wheel by a ratched wheel with pawl.

8. A suction injector as defined in claim 1, wherein the connection means between said other end of said taster finger and a lever for blocking of a gear with the function of said means for blocking and warning is a Bowden cable.

9. A suction injector as defined in claim 1, wherein said axis rod has rings for marking the extent of the backward movement after the use as means of self-control.

10. A suction injector as defined in claim 1, wherein said motor is a electrical motor connected with batteries as said power source; driving a hose pump as said compressing means to regulate the stream of said liquid; while the dosing is brought about by an electronic steering-unit; inside of said suction cup being an electrical contact serving as means corresponding to a firm skin contact for activating of the hose pump regulated by said electronic steering-unit; and a counter as means for blocking and marking said blocking of the function of said injector, if the liquid supply into said container with hose is nearly exhausted.

11. A suction injector as defined in claim 10, wherein inside of said suction cup are two pipes for the cannula attachment adjointed to two liquid containers through two hoses; said two pipes being coordinated to two electrical contacts cooperating in the choice of dosing program of said electronic steering-unit to coordinate the chosen liquid container and cannula attachment pipe.

12. A suction injector as defined in claim 1+10, wherein two dosing wheels are driven by motor using a gear-shifting pinion as coupling between said motor and said the hose pump.

13. A suction injector as defined in claim 1+10, wherein said suction source is a compressor driven by a electrical motor.

14. A suction injector as defined in claim 1+10, wherein said triggering means corresponding to firm skin contact of said suction cup are electrical contacts allocated along the circumference of said suction cup nearly to the rim of this to trigger the function of the compressor; a further electrical contact being inside of said suction cup to trigger the function of said hose pump.

15. A suction injector as defined in claim 10, wherein said electrical contact for activating said hose pump is a earth contact circuit arrangement.

16. A suction injector as defined in claim 1, wherein a nozzle communicates with said suction cup for reventilation.

17. A suction injector as defined in claim 1, wherein a container is provided for storing the underpressure in a tubular connection to said suction cup.

18. A suction injector as defined in claim 1, wherein the housing of the injector is said container.

19. A suction injector as defined in claim 1, wherein as said vacuum source a outer chamber of said suction cup with stored underpressure is replacable connected by a central conical opening of his covering lid to the attachment pipe of the injector and firmly fastened at his central covering part arround a smaller inner portion with cannula shaft, and valve means are used between the outer chamber and the inner portion, which expands upwards, if the skin is pressed against the rim of said suction cup and activates the valve means.

20. A suction injector as defined in claim 1+18, wherein said covering part has a boring to said inner portion for detecting the opening of said valve.

21. A suction injector as defined in claim 18, wherein said central covering part has inside of said central conical opening a boring to said inner portion for reventilation, in the case that the attachment pipe is removed from said central conical opening.

22. A suction injector as defined in claim 18, wherein said outer chamber has a boring, which runs horizontally through the outer wall and is closed by a membrane, which may be removed for reventilation.

23. A suction injector as defined in claim 1, wherein said liquid container with a folding bellows as said pressurized gas compartment with longitudinal conduits is provided between the liquid container and the folded bellows to facilitate said liquid emtying from the folds of the folded bellows.

24. A suction injector as defined in claim 1, wherein said liquid container has a basin opposite to the collar for the outlet of the hose to take up the collar with the hose and the clip and the connection fitting of another liquid container of the same kind.

25. A suction injector as defined in claim 1, wherein said liquid container which may have a membraneous wall has a membraneous bag with said liquid inside connected to said hose.

26. A suction injector as defined in claim 1+15, wherein said nozzle is replaced by a body semipermeable for air.

* * * * *